(12) United States Patent
Wang et al.

(10) Patent No.: US 9,011,890 B2
(45) Date of Patent: Apr. 21, 2015

(54) ANTIBACTERIAL SOL-GEL COATING SOLUTION

(75) Inventors: De-xian Wang, Qin Huang Dao (CN); Zhen-yu Lei, Qin Huang Dao (CN)

(73) Assignee: Qinhuangdao Yipeng Special Glass Co., Ltd., Qin Huang Dao (CN)

( * ) Notice: Subject to any disclaimer, the term of this patent is extended or adjusted under 35 U.S.C. 154(b) by 1275 days.

(21) Appl. No.: 12/097,123

(22) PCT Filed: Dec. 12, 2005

(86) PCT No.: PCT/CN2005/002153
§ 371 (c)(1),
(2), (4) Date: Jun. 12, 2008

(87) PCT Pub. No.: WO2007/068140
PCT Pub. Date: Jun. 21, 2007

(65) Prior Publication Data
US 2008/0305153 A1    Dec. 11, 2008

(51) Int. Cl.
*A61K 9/70* (2006.01)
*C09D 1/00* (2006.01)
*A01N 59/16* (2006.01)
*C03C 17/00* (2006.01)
*C03C 17/25* (2006.01)
*C09D 5/14* (2006.01)
*B05D 5/00* (2006.01)

(52) U.S. Cl.
CPC *C09D 1/00* (2013.01); *A01N 59/16* (2013.01); *C03C 17/007* (2013.01); *C03C 17/25* (2013.01); *C03C 17/256* (2013.01); *C03C 2204/02* (2013.01); *C03C 2217/212* (2013.01); *C03C 2217/213* (2013.01); *C03C 2217/475* (2013.01); *C03C 2217/477* (2013.01); *C03C 2218/113* (2013.01); *C09D 5/14* (2013.01)

(58) Field of Classification Search
CPC ....... A61K 33/34; A61K 47/02; A61K 33/38; A61K 9/08; A61K 9/70; C03C 17/22; C03C 2217/475; C03C 2217/477; C03C 2217/212; C03C 2217/213; C03C 2204/02; C03C 17/007; C03C 17/25; C03C 17/256; B05D 5/00; C09D 5/025; C09D 1/00; C09D 5/14; A01N 59/16
USPC ............................ 516/33; 106/287.16, 287.19
See application file for complete search history.

(56) References Cited

U.S. PATENT DOCUMENTS

| | | | | |
|---|---|---|---|---|
| 5,755,867 | A * | 5/1998 | Chikuni et al. | 106/287.16 |
| 5,897,958 | A * | 4/1999 | Yamada et al. | 502/242 |
| 6,294,247 | B1 * | 9/2001 | Watanabe et al. | 428/312.8 |
| 6,765,721 | B2 * | 7/2004 | Kawazu et al. | 359/492 |
| 6,797,278 | B2 * | 9/2004 | Jackson et al. | 424/405 |
| 2002/0122962 | A1 * | 9/2002 | Arfsten et al. | 428/697 |
| 2003/0118733 | A1 * | 6/2003 | Jackson et al. | 427/372.2 |
| 2003/0167878 | A1 | 9/2003 | Al-Salim et al. | |
| 2003/0235653 | A1 * | 12/2003 | Yu | 427/376.2 |

FOREIGN PATENT DOCUMENTS

| | | | |
|---|---|---|---|
| CN | 1370752 | | 9/2002 |
| CN | 1583636 | | 2/2005 |
| CN | 1597810 | | 3/2005 |
| CN | 1676226 | | 10/2005 |
| CN | 1676226 A | * | 10/2005 |
| CN | 1676227 A | * | 10/2005 |
| JP | 2002188054 A | * | 7/2002 |
| JP | 2002-338302 A | * | 11/2002 |
| JP | 2004161573 A | * | 6/2004 |
| JP | 2005-279582 A | * | 10/2005 |
| KR | 2005049446 A | * | 5/2005 |

OTHER PUBLICATIONS

Derwent Abstract on EAST, week 200751, London: Derwent Publications Ltd., AN 2006-137761, Class D22, CN 1676226 A, (Taixin Ceramic Co Ltd Hunan Prov), abstract.*
Human Assisted Machine Translation to English of CN 1676226 A (application published Oct. 5, 2005), Obtained online @ https://cs.dialog.com/client/csc_sh127/ , (downloaded Jan. 24, 2011), pp. 1-3.*
Derwent Abstract, week 200807, London: Derwent Publications Ltd., AN 2004-491337, Class D22, JP 2004161573 A, (Nihon Parkerising Co Ltd), abstract.*
Derwent Abstract, week 200759, London: Derwent Publications Ltd., AN 2006-137762, Class D22, CN 1676227 A (Taixin Ceramic Ind Co Ltd), abstract.*
Translation of 102005KR-032967 (KR 2005049446 A—Published May 25, 2005) Korean Patent Office, obtained online @ http://kposd.kipo.go.kr:8088/up/kpion/ (Downloaded Jan. 26, 2011).*
Derwent Abstract, week 200144, London: Derwent Publications Ltd., AN 2004-409459, Class A60, CN 1286915 A (Taixing Nanometer Material Factory Inst), abstract.*
Derwent Abstract, week 200144, London: Derwent Publications Ltd., AN 2001-409516, Class E32, CN 1287138 A (Taixing Nanometer Level Material Plant I), abstract.*
Derwent Abstract, week 200845, London: Derwent Publications Ltd., AN 2004-441767, Class L01, CN 1488596 A (Hunan Taixin Ceramics Co Ltd), abstract.*
Human Assisted Machine Translation to English of CN 1676227 A (application published Oct. 5, 2005), Obtained online @ https://cs.dialog.com/client/csc_sh127/ , (downloaded Jan. 25, 2011), pp. 1-3.*
Derwent Abstract, week 200763, London: Derwent Publications Ltd., AN 2006-195378, Class E12, CN 1693250 A (Taixin Ceramic Co Ltd Hunan Prov), abstract.*
Derwent Abstract, week 200648, London: Derwent Publications Ltd., AN 2006-468972, Class J04, KR 2005049446 A (Kim M C), abstract.*

(Continued)

*Primary Examiner* — Daniel S Metzmaier
(74) *Attorney, Agent, or Firm* — Knobbe Martens Olson & Bear LLP

(57) ABSTRACT

Antibacterial sol-gel coating solutions are used to form articles. The antibacterial sol-gel coating solution includes at least one Ti or Si-containing compound that is capable of hydrolyzing to form a base film; a regulating agent capable of regulating the hydrolysis rate of the Ti or Si-containing compounds, an organic solvent, water, and at least one soluble compound of an antibacterial metal, such as Ag, Cu, Mg, Zn, Sn, Fe, Co, Ni, or Ce.

8 Claims, 2 Drawing Sheets

(56) References Cited

OTHER PUBLICATIONS

Kim et al., Hydrothermal Synthesis of Titanium Dioxide Using Acid Peptizing Agents and Their Photocatalytic Activity, Korean J. Chem. Eng., 22(3), 370-374 (May 2005), obtained online @ http://210.101.116.28/W_kiss2/03421049_pv.pdf (Downloaded Jan. 27, 2011).*

JPO on EAST, Patent Abstracts of Japan, Japan patent Office, Tokyo, Japan, JP 2002338302 A (Nov. 2002), Abstract.*

Machine Translation of Publ. No. JP 2002-338302, published Nov. 2002, Japan patent Office, Tokyo, Japan, obtained online @ http://dossier1.ipdl.inpit.go.jp/AIPN/odse_top_dn.ipdl?N0000=7400 (Downloaded Mar. 17, 2014).*

JPO on EAST, Patent Abstracts of Japan, Japan patent Office, Tokyo, Japan, JP 2002188054 A (Jul. 2002), Abstract.*

Machine Translation of Publ. No. JP 2002-188054, published Jul. 2002, Japan patent Office, Tokyo, Japan, obtained online @ http://dossier1.ipdl.inpit.go.jp/AIPN/odse_top_dn.ipdl?N0000=7400 (Downloaded Mar. 17, 2014).*

JPO on EAST, Patent Abstracts of Japan, Japan patent Office, Tokyo, Japan, JP 2005279582 A (Oct. 2005), Abstract.*

Machine Translation of Publ. No. JP 2005-279582, published Oct. 2005, Japan patent Office, Tokyo, Japan, obtained online @ http://dossier1.ipdl.inpit.go.jp/AIPN/odse_top_dn.ipdl?N0000=7400 (Downloaded Mar. 17, 2014).*

Pastoriza-Santos et al., "One-Pot Synthesis of Ag@TiO2 Core-Shell Nanoparticles and Their Layer-by-Layer Assembly", Langmuir, (2000) 16, pp. 2731-2735 (Publ. on web: Jan. 26, 2000).*

Machine Translation of Publ. No. JP 2002188054 A, published Jul. 2002, Japan patent Office, Tokyo, Japan, obtained online @ http://dossier1.ipdl.inpit.go.jp/AIPN/odse_top_dn.ipdl?N0000=7400 (Downloaded Nov. 1, 2014), pp. 1-12.*

* cited by examiner

_US 9,011,890 B2_

ANTIBACTERIAL SOL-GEL COATING SOLUTION

TECHNICAL FIELD

The present invention relates to an antibacterial sol-gel coating solution, a process for preparing said solution, an antibacterial article, and a process and apparatus for producing said article.

BACKGROUND OF THE INVENTION

In response to the ever-increasing human demand for quality life, antibacterial material and article industry has become a substantial trade, serving people in multiple aspects of daily life. For example, antibacterial materials, clothes and paints, which offer convenience and advantages, have been developed.

In the manufacture of antibacterial materials and articles, an antibacterial agent with various functions is usually prepared from an inorganic antibacterial agent, such as a nontoxic inorganic salt of Ag, Cu, Zn and the like, by wrapping, dispersing or introducing in other ways the salt into a matrix of an inorganic nonmetal material (e.g. $SiO_2$ and the like). The antibacterial agent is in turn dispersed onto the surface of a substrate, thus producing a contact-type antibacterial material or article.

In making antibacterial articles with hard substrates, such as metals, ceramics, glass and rigid plastics, by means of adding antibacterial agent, however, the amount of the antibacterial agent added may be limited by the nature of these substrates. As a result, such addition may produce an antibacterial article with a low concentration of the antibacterial agent, which displays a low level of antibacterial property. Additionally, the antibacterial agent is difficult to disperse evenly, resulting in unstable antibacterial effect on the surface of the article. Furthermore, the antibacterial agent may be reduced and inactivated during high-temperature processing of such substrates.

Therefore, for hard substrates, there is a need for providing an antibacterial coating solution which can increase the amount of the antibacterial agent added, enhancing the concentration of the agent on the surface of the substrate, thus improving the antibacterial property of the resulting article, especially a contact-type antibacterial article.

SUMMARY OF THE INVENTION

The inventors have found that an antibacterial sol-gel coating solution of the present invention makes it possible to produce, in a simple process, an article with a hard material substrate which shows good antibacterial property. The inventors have further found that said antibacterial sol-gel coating solution can also makes it possible to produce, in a simple process, an article with a substrate of medium or even lower surface hardness which shows good antibacterial property.

Therefore, one object of the invention is to provide an antibacterial sol-gel coating solution, comprising a. at least one substance selected from the group consisting of Ti- or Si-containing compounds capable of hydrolyzing to form a base film;

b. a regulating agent capable of regulating the hydrolysis rate of the Ti- or Si-containing compounds;

c. an organic solvent;

d. water; and e. at least one soluble compound of an antibacterial metal, said antibacterial metal being selected from the group consisting of Ag, Cu, Mg, Zn, Sn, Fe, Co, Ni, and Ce; wherein a, b and a portion of c are first mixed to form a solution I, then d and the rest of c are mixed and added into solution I to form a dispersion II, and finally e is added into dispersion II to form the antibacterial sol-gel coating solution.

Another object of the invention is to provide a process for preparing an antibacterial sol-gel coating solution, comprising the steps of (1) dissolving, in at least one organic solvent, at least one substance selected from the group consisting of Ti- or Si-containing compounds capable of hydrolyzing to form a base film, and a regulating agent capable of regulating the hydrolysis rate of the Ti- or Si-containing compounds to form a solution I;

(2) mixing at least one organic solvent with water and adding the resulting mixture into solution I to form a dispersion II;

(3) adding at least one soluble compound of an antibacterial metal into dispersion II to form the antibacterial sol-gel coating solution, said antibacterial metal being selected from the group consisting of Ag, Cu, Mg, Zn, Sn, Fe, Co, Ni, and Ce.

Yet another object of the invention is to provide an antibacterial article, which comprises a substrate and an antibacterial layer on at least one surface thereof, said antibacterial layer comprising at least one element selected from the group consisting of Ti and Si, and at least one antibacterial metal selected from the group consisting of Ag, Cu, Mg, Zn, Sn, Fe, Co, Ni, and Ce.

Still another object of the invention is to provide a process for producing an antibacterial article, comprising the steps of applying the antibacterial sol-gel coating solution onto at least one surface of a substrate to form a coating or coatings, and subjecting the coating(s) to drying and thermal treatment. The process of the present invention requires only simple operations at low cost and thus can be carried out easily.

Still another object of the present invention is to provide an apparatus for producing an antibacterial article, said apparatus comprising a dip coater system and a thermal treatment furnace, wherein the dip coater system is suitable to coat a substrate with an antibacterial sol-gel coating solution to form a coating or coating(s) on the surface of the substrate.

DETAILED DESCRIPTION OF THE INVENTION

Figure 1:
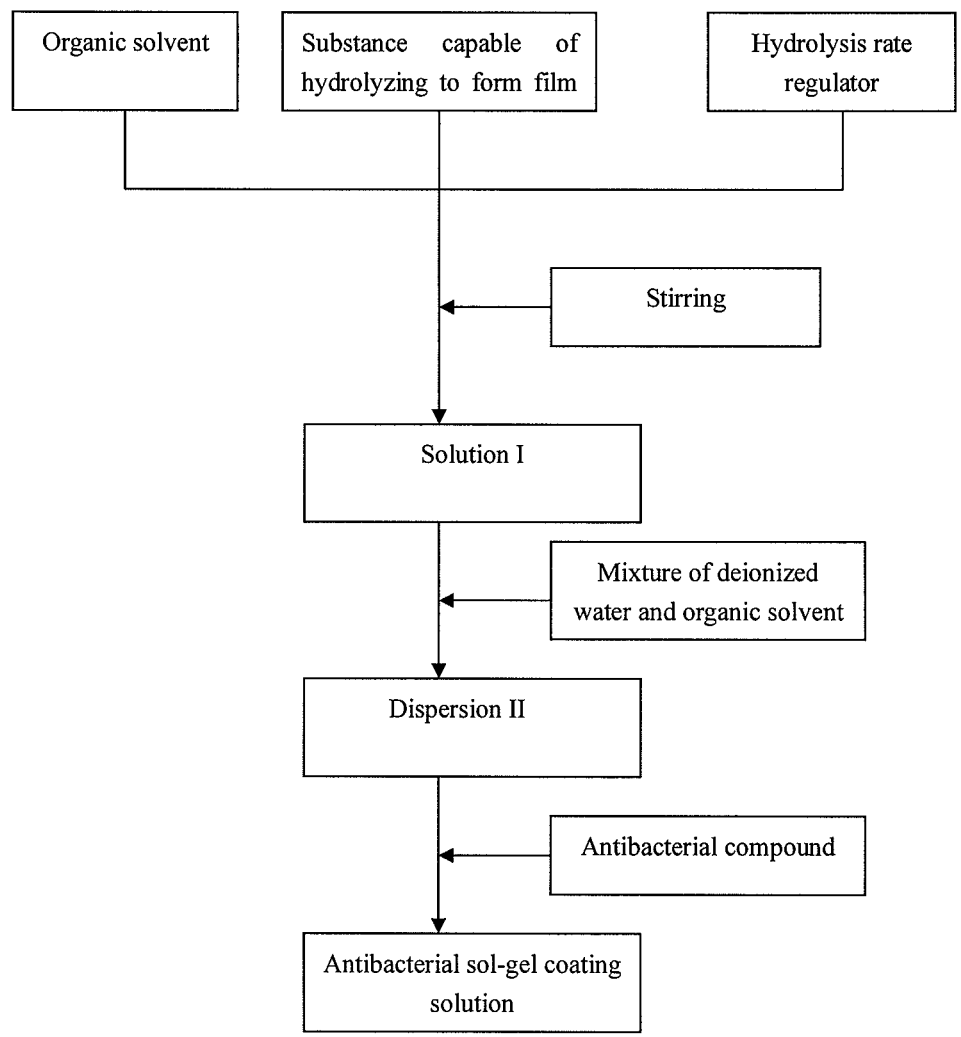
FIG. 1 is a schematic diagram showing a process for preparing an antibacterial sol-gel coating solution according to one embodiment of the invention.

As used herein, the sol-gel coating solution refers to a coating solution defined according to the present invention suitable for dip-coating technique, in the form of dispersion.

As used herein, the word "a", "an" or "the" may include both singular and plural referents, wherever such a word exist or does not exist before a noun. Thus, for example, "c. an organic solvent" in the antibacterial sol-gel coating solution of the present invention includes one or more organic solvents.

The antibacterial sol-gel coating solution of the present invention comprises a. at least one substance selected from the group consisting of Ti- or Si-containing compounds capable of hydrolyzing to form a base film;

b. a regulating agent capable of regulating the hydrolysis rate of the Ti- or Si-containing compounds;

c. an organic solvent;

d. water; and e. at least one soluble compound of an antibacterial metal, said antibacterial metal being selected from the group consisting of Ag, Cu, Mg, Zn, Sn, Fe, Co, Ni, and Ce;

wherein a, b and a portion of c are first mixed to form a solution I, then d and the rest of c are mixed and added into solution I to form a dispersion II, and finally e is added into dispersion II to form the antibacterial sol-gel coating solution.

In a preferred embodiment of the present invention, the antibacterial sol-gel coating solution comprises, based on total weight of the solution, 0.1-456, preferably 1-35% and more preferably 2-25% of at least one substance selected from the group consisting of Ti- or Si-containing compounds capable of hydrolyzing to form a base film. In a specific embodiment of the present invention, as the Ti- or Si-containing compounds capable of hydrolyzing to form a base film, the Ti-containing compounds can be, for example, butyl titanate ($Ti(OC_4H_9)_4$), isobutyl titanate ($Ti[OCH_2CH(CH_3)_2]_4$), ethyl titanate ($Ti(OC_2H_5)_4$), n-propyl titanate ($Ti(OC_3H_7)_4$), isopropyl titanate ($Ti[OCH(CH_3)_2]_4$), titanium tetrachloride ($TiCl_4$), titanium trichloride ($TiCl_3$), or titanium dioxide nanoparticle or the like, and the Si-containing compounds can be, for example, tetraethyl orthosilicate ($Si(OC_2H_5)_4$), tetramethyl orthosilicate ($Si(OCH_3)_4$), tetrapropyl orthosilicate ($Si(OC_3H_7)_4$), tetrabutyl silicate ($Si(OC_4H_9)_4$), tetraisopropyl orthosilicate ($Si[OCH(CH_3)_2]_4$), tetraisobutyl silicate ($Si[OCH_2CH(CH_3)_2]_4$) or the like. These compounds can be used alone or in combination. When the Ti- or Si-containing compounds are used in combination, their total content in the antibacterial sol-gel coating solution is in the range of 0.1-45%, preferably 1-35% and more preferably 2-25%.

In a preferred embodiment of the present invention, the antibacterial sol-gel coating solution comprises, based on total weight of the solution, 0.001-25%, preferably 0.01-20% and more preferably 0.1-18% of a regulating agent capable of regulating the hydrolysis rate of the Ti- or Si-containing compounds (also referred to as "a hydrolysis rate regulator" herein). The hydrolysis rate regulator is responsible for regulating the hydrolysis rate of at least one substance selected from the group consisting of Ti- or Si-containing compounds capable of hydrolyzing to form a base film, so that the hydrolysis is carried out in a controllable manner. In a preferred embodiment of the present invention, the hydrolysis rate regulator is, for example, diethanolamine ($HN(CH_2CH_2OH)_2$), hydrochloric acid (HCl), nitric acid ($HNO_3$), sulfuric acid ($H_2SO_4$), acetylacetone (AcAc, $CH_3COCH_2COCH_3$), tartaric acid ($C_4H_6O_6$), citric acid ($C_6H_8O_7.H_2O$), cinnamic acid ($C_9H_8O_2$), perchloric acid ($HClO_4$), phosphoric acid ($H_3PO_4$), triethanolamine ($N(CH_2CH_2OH)_3$), ethanolamine ($H_2NCH_2CH_2OH$), ethylene diamine ($H_2NCH_2CH_2NH_2$), acetic acid (HAc, $CH_3COOH$), dimethyl formamide ($HCON(CH_3)_2$), aqueous ammonia ($NH_3.H_2O$), diethylamine ($(C_2H_5)_2NH$) and triethylamine ($(C_2H_5)_3N$) and the like.

In the present invention, based on total weight of the coating solution, the contents of the organic solvent and the other components in the antibacterial sol-gel coating solution add up to 100%. In a preferred embodiment of the invention, the organic solvent is, for example, diethyl ether ($C_2H_5OC_2H_5$), acetone ($CH_3COCH_3$), isopropanol ($(CH_3)_2CHOH$), propanol ($C_3H_7OH$), ethanol ($C_2H_5OH$), methanol ($CH_3OH$), butanol ($C_4H_9OH$), isobutanol ($(CH_3)_2CHCH_2OH$) and ethylene glycol ($OHCH_2CH_2OH$) and the like. Each of these organic solvents can be used alone or in combination.

In a preferred embodiment of the present invention, the antibacterial sol-gel coating solution comprises, based on total weight of the solution, 0.001-15%, preferably 0.01-120 and more preferably 0.1-10% of deionized water.

In a preferred embodiment of the present invention, the antibacterial sol-gel coating solution comprises, based on total weight of the solution, 0.001-25%, preferably 0.01-20% and more preferably 0.1-15 of at least one soluble compound of antibacterial metal, said antibacterial metal being selected from the group consisting of Ag, Cu, Mg, Zn, Sn, Fe, Co, Ni, and Ce. In a preferred embodiment of the present invention, the soluble compound of antibacterial metal is, for example, $AgNO_3$, $Ag+HNO_3$, $Ag_2AsO_4$ (silver arsenate), $AgClO_3$ (silver chlorate), $C_3H_5AgO_3H_2O$ (silver lactate), $AgClO_4$ (silver perchlorate), $Ag_2Cr_2O_7$ (silver dichromate), $Cu(CH_3COO)_2 H_2O$ (copper acetate), $CuBr_2$ (copper bromide), $C_{24}H_{26}CuO_8$ (Butyl Phthalate Copper), $CuCl_2.2H_2O$ (cupric chloride), $CuCl_2$ (anhydrous cupric chloride), $Cu(AcAc)_2$ (Copper acetylacetonate), $Cu_2Cr_2O_7.2H_2O$ (cupric dichromate), $CuF_2.2H_2O$ (cupric fluoride), $Cu(NO_3)_2.3H_2O$ (cupric nitrate), $Mg(CH_3COO)_2.4H_2O$ (magnesium acetate), $MgBr_2$ (magnesium bromide), $MgCl_2$ (magnesium chloride), $MgI_2$ (magnesium iodide), $Mg(NO_3)_2$ (magnesium nitrate), $MgSO_4$ (magnesium sulfate), $SnCl_2$ (anhydrous tin dichloride), $SnCl_2.2H_2O$ (tin dichloride), $SnCl_4-5H_2O$ (tin tetrachloride), $SnCl_4$ (anhydrous tin tetrachloride), $SnI_4$ (tin tetraiodide), $SnBr_4$ (tin tetrabromide), $SnBr_2.2H_2O$ (tin dibromide), $Fe(OH)(CH_3COO)_3$ (basic ferric acetate), $FeBr_3$ (ferric bromide), $FeCl_3$ (anhydrous ferric trichloride), $FeCl_3.6H_2O$ (ferric trichloride hexahydrate), $Fe(NO_3)_3.9H_2O$ (ferric nitrate), $Fe(C_7H_{15}COO)_3$ (ferric octoate), $Fe(AcAc)_2$ (ferric acetylacetonate), $FeBr_2.4H_2O$ (ferrous bromide), $FeCl_2.4H_2O$ (ferrous chloride), $FeI_2.4H_2O$ (ferrous iodide), $ZnCl_2$ (zinc chloride), $Zn(CH_3COO)_2.2H_2O$ (zinc acetate), $Zn(NO_3)_2.6H_2O$ (zinc nitrate), $Zn(C_3H_5O_2)_2$ (zinc propionate) $Zn[C_6H_4 (OH)COO]_2.3H_2O$ (zinc salicylate), $Zn(C_5H_9O_2)_2.2H_2O$ (zinc pentanoate), $Co(NO_3)_2.6H_2O$ (cobalt nitrate), $CoCl_2.6H_2O$ (cobalt chloride), $Co(CH_3COO)_2.4H_2O$ (cobalt acetate), $Co(AcAc)_2$ (cobalt acetylacetonate), $CoSO_4.7H_2O$ (cobalt sulfate), $Ni(CH_3COO)_2.4H_2O$ (nickel acetate), $NiBr_2.3H_2O$ (nickel bromide), $NiCl_2.6H_2O$ (nickel chloride), $NiI_2.6H_2O$ (nickel iodide), $Ni(NO_3)_2. 6H_2O$ (nickel nitrate), $NiSO_4.7H_2O$ (nickel sulfate), $CeBr_3.7H_2O$ (cerium bromide), $CeCl_3.7H_2O$ (cerium chloride), $Ce(NO_3)_2.6H_2O$ (cerium nitrate) and $(NH_4)_2Ce(NO_3)_6$ (ammonium cerium nitrate). It is to be understood that the "soluble compound of antibacterial metal" can be added in any form, for example, as "$Ag+ HNO_3$", provided that it is dispersible in the antibacterial sol-gel coating solution of the present invention. Each of these compounds of antibacterial metal can be used separately or in combination.

In step (1) of the process for preparing the antibacterial sol-gel coating solution of the present invention, at least one substance selected from the group consisting of Ti- or Si-containing compounds capable of hydrolyzing to form a base film, and a regulating agent capable of regulating the hydrolysis rate of the Ti- or Si-containing compounds are dissolved into at least one organic solvent, optionally with stirring, to form solution I. Said at least one substance is added at an amount sufficient to achieve a final concentration of 0.1-45%, preferably 1-356, and more preferably 2-25%, based on the antibacterial sol-gel coating solution (the same for other components). The hydrolysis rate regulator is added at an amount sufficient to achieve a final concentration of 0.001-25%, preferably 0.01-20%, and more preferably 0.1-18%.

In step (2), at least one organic solvent is mixed with water to form a mixture, which is in turn added into solution I, optionally with stirring, to form dispersion II. The organic solvent(s) used in step (2) can be the same or different from that used in step (1) for forming solution I, but preferably, the same. In step (2), the weight ratio of the organic solvent(s) to water is in the range of 1:0.0001-20, preferably 1:0.005-15, more preferably 1:0.01-12, and most preferably 1:0.1-10.

The weight ratio of the organic solvent(s) used in step (2) to that used in step (1) is in the range of 1:0.1-30, preferably 1:0.5-20, and more preferably 1:5-15.

In step (3), at least one soluble compound of antibacterial metal is added into dispersion II to form the antibacterial sol-gel coating solution, said antibacterial metal being selected from the group consisting of Ag, Cu, Mg, Zn, Sn, Fe, Co, Ni, and Ce. The addition is carried out optionally with stirring. The amount of the soluble compound of antibacterial metal added is sufficient to achieve a final concentration of 0.001-25%, preferably 0.01-20%, and more preferably 0.1-15% in the antibacterial sol-gel coating solution.

The resulting antibacterial sol-gel coating solution is preferably allowed to stand for 0.5-48 hr, more preferably 5-24 hr, and most preferably 10-18 hr before use.

The antibacterial sol-gel coating solution of the present invention can be applied on the following substrates to form an antibacterial layer, thus producing an antibacterial article: sheet or profiled glass, and products thereof; architectural or decorative ceramics, and products thereof; stone materials and products thereof; sheet or profiled metal, and products thereof; and sheet or profiled plastics, and products thereof. These substrates in any shape can be treated with the antibacterial sol-gel coating solution of the present invention to form an antibacterial layer.

The antibacterial article of the present invention comprises a substrate and an antibacterial layer on at least one surface thereof. Said antibacterial layer comprises at least one element selected from the group consisting of Ti and Si, and at least one antibacterial metal selected from the group consisting of Ag, Cu, Mg, Zn, Sn, Fe, Co, Ni, and Ce.

In a preferred embodiment of the present invention, the antibacterial layer of the antibacterial article of the present invention has a thickness of 5-800 nm, preferably 10-600 nm, and more preferably 20-500 nm. The antibacterial layer comprises, based on its weight, 10-90%, preferably 20-80% and more preferably 35-65% of at least one matrix selected from the group consisting of $SiO_2$ and $TiO_2$, and 10-90%, preferably 20-80% and more preferably 35-65% of at least one compound of antibacterial metal selected from the group consisting of Ag, Cu, Mg, Zn, Sn, Fe, Co, Ni, and Ce. The thickness of the antibacterial layer can be measured by, for example, a gauge-meter or a scanning electron microscope. The contents of the matrix and the compound of antibacterial metal in the antibacterial layer can be determined by calculating their respective changes between the substrate to be coated and the coated substrate.

The antibacterial article of the present invention can be used for medical and health service in e.g. an medical operation room, a laboratory, a ward, a pharmacy, an operating board, a medicine locker, an instrument cabinet and the like; in foodstuff and pharmacy industries in e.g. a dust proof workshop, a dining room and a food locker; in traffic and transportation, furniture and home decoration, household appliances, construction, etc. They help reduce labour and maintenance cost.

To produce the antibacterial article of the present invention, a substrate is put into the coating solution. Where necessary, the substrate is covered by a protective mask on one surface or part of the surface before being put into the coating solution, so that it is contacted and reacted with the solution in a desired position to obtain a desired pattern. The substrate is contacted with the coating solution at ambient temperature, or at a temperature of, for example, 5-80° C., preferably 20-50° C., and more preferably 25-30° C., where the nature of the antibacterial sol-gel coating solution will not be changed. The contacting of the substrate with the coating solution is carried out under atmospheric pressure, or under increased pressure, for example, 1.5-3.5 atm, and preferably 2 atm, to prevent the evaporation of the solvent from the antibacterial sol-gel coating solution. The substrate is contacted with the coating solution for a period of generally 1-40 seconds, preferably 2-30 seconds, and more preferably 5-10 seconds.

After being contacted with the coating solution, the substrate is drawn out from the solution and allowed to stand in air for 1-15 min, preferably 3-10 min and more preferably 5-7 min. It is then subjected to thermal treatment at a temperature of 80-850° C. preferably 120-800° C. and more preferably 150-700° C. for a period of 10-600 min, preferably 20-450 min and more preferably 30-300 min, to form an antibacterial layer. As recognized by a person skilled in the art, the temperature for thermal treatment varies depending on the substrate to be treated, and should be the one where the nature of the substrate will not be changed. The temperature can be determined by a person skilled in the art through routine experimentation or according to available information concerning the substrate.

The apparatus for producing the antibacterial article of the present invention comprises a dip coater system and a thermal treatment furnace, wherein the dip coater system is suitable to apply an antibacterial sol-gel coating solution to a substrate. Said dip coater system is suitable to contain the antibacterial sol-gel coating solution and to keep it stable in terms of its performance. The thermal treatment furnace is a device for thermal treatment, in which temperature-controlling means is provided.

The invention will be described in more detail with reference to the accompanying drawings and some embodiments. It should be appreciated that these embodiments shall never be construed as limiting the invention.

As shown in FIG. 1, at a temperature of 10-30° C. and a relative humidity lower than 80%, a Ti or Si-containing compound capable of hydrolyzing to form a base film and a hydrolysis rate regulator are mixed with an organic solvent, optionally with stirring, to form a solution I. A mixture of water and an organic solvent is then added to solution I to form a dispersion II, to which an antibacterial compound is added to form the antibacterial sol-gel coating solution.

Figure 2:
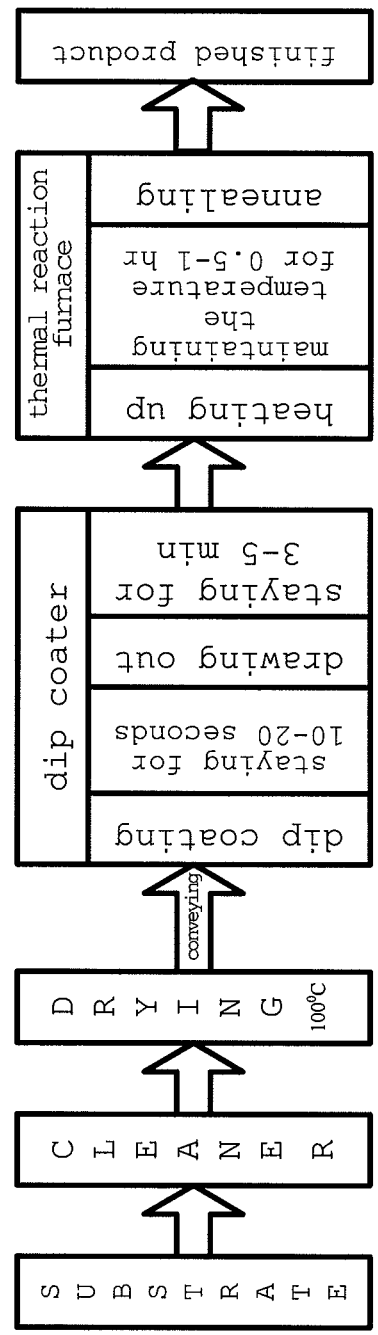
FIG. 2 is a schematic diagram showing a process for producing an antibacterial article according to one embodiment of the invention.

As shown in FIG. 2, a substrate (cleaned and dried beforehand when necessary) is put into a dip coater, and kept in contact with an antibacterial sol-gel coating solution for 10-20 seconds. After being drawn out, the coated substrate is allowed to stand in air for 3-5 min, and conveyed into a thermal treatment furnace and subjected to thermal treatment for 0.5-1 hr, which is then cooled (annealed) to obtain the finished product.

The invention will now be described in more detail with reference to examples. These examples are intended to be illustrative, without any limitation to the invention.

Example 1

In this Example, an antibacterial sol-gel coating solution was prepared using $Ti(OC_4H_9)_4$ as substance capable of hydrolyzing to form a base film, $NH(C_2H_4OH)_2$ as hydrolysis rate regulator, $C_2H_5OH$ as solvent, and $AgNO_3$ as antibacterial compound.

28% of $Ti(OC_4H_9)_4$, 1% of $NH(C_2H_4OH)_2$ and 50% of $C_2H_5OH$, all based on the weight of the final antibacterial sol-gel coating solution (the same hereinafter), were mixed to form a solution I. 2% of de-ionized water and 9% of $C_2H_5OH$ were then mixed and added into solution I to form a dispersion II, to which 10% of $AgNO_3$ was added. The mixture was stirred for 1 hr to obtain a uniform and transparent antibacterial sol-gel coating solution.

Example 2

In this Example, an antibacterial sol-gel coating solution was prepared using $Si(OC_4H_9)_4$ as substance capable of hydrolyzing to form a base film, $C_2H_5OH$ as solvent, HAc as hydrolysis rate regulator, and $AgNO_3$ as antibacterial compound.

40% of $Si(OC_4H_9)_4$, 40% of $C_2H_5OH$ and 2% of HAc were mixed to form a solution I. 3% of deionized water and 12% of $C_2H_5OH$ were then mixed and added into solution I to form a dispersion II, to which 3% of $AgNO_3$ was added. The mixture was stirred for 1.5 hr to obtain a uniform and transparent antibacterial sol-gel coating solution.

Example 3

In this Example, an antibacterial sol-gel coating solution was prepared using $Ti(OC_2H_5)_4$ as substance capable of hydrolyzing to form a base film, $C_2H_5OH$ as solvent, $HCON(CH_3)_2$ as hydrolysis rate regulator, and $Cu(NO_3)_2$ as antibacterial compound.

33% of $Ti(OC_2H_5)_4$, 4% of $HCON(CH_3)_2$ and 31% of $C_2H_5OH$ were mixed to form a solution I. 4% of deionized water and 12% of $C_2H_5OH$ were then mixed and added into solution I to form a dispersion II, to which 16% of $Cu(NO_3)_2$ was added. The mixture was stirred for 0.5 hr to obtain a uniform and transparent antibacterial sol-gel coating solution.

Example 4

In this Example, an antibacterial sol-gel coating solution was prepared using $Si(OC_2H_5)_4$ as substance capable of hydrolyzing to form a base film, $C_2H_5OH$ as solvent, AcAc as hydrolysis rate regulator, and $Cu(NO_3)_2$ as antibacterial compound.

32% of $Si(OC_2H_5)_4$, 38% of $C_2H_5OH$ and 7% of AcAc were mixed to form a solution I. 2% of deionized water and 9% of $C_2H_5OH$ were then mixed and added into solution I to form a dispersion II, to which 12% of $Cu(NO_3)_2$ was added. The mixture was stirred for 1 hr to obtain a uniform and transparent antibacterial sol-gel coating solution.

Example 5

Under the conditions listed in Table 1, four sheets of glass substrate (50×50 mm, with a thickness of 5 mm) with clean surfaces were dipped into 300 ml of the antibacterial sol-gel coating solutions from Examples 1-4 respectively, in a dip coater at ambient temperature under atmospheric pressure, to form a coating layer. The substrates were then dried in air for 10 min and subjected to thermal treatment to obtain antibacterial articles.

The thickness of the layer on each of the resulting antibacterial articles was measured by a gauge-meter or a scanning electron microscope (SEM), and the change of the content of each ingredient between the substrate to be coated and the coated substrate was recorded to determine the amount of the ingredient introduced into the coating layer. The results were listed in Table 1.

TABLE 1

| | | glass 1# | glass 2# | glass 3# | glass 4# |
|---|---|---|---|---|---|
| Sample number coating solution | | Example 1 | Example 2 | Example 3 | Example 4 |
| dip coating time (seconds) | | 30 | 30 | 30 | 30 |
| thermal treatment | temperature (° C.) | 500 | 500 | 500 | 500 |
| | time (hour) | 1 | 1 | 1 | 1 |
| coating | thickness (nm) | 150 | 310 | 180 | 250 |
| Composition (wt. %) | Film carrier | $TiO_2$ (48.48%) | $SiO_2$ (77.07%) | $TiO_2$ (67.47%) | $SiO_2$ (66.79%) |
| | Antibacterial ion | $Ag^+$ (48.05%) | $Ag^+$ (21.39%) | $Cu^{2+}$ (25.98%) | $Cu^{2+}$ (26.53%) |

Example 6

Under the conditions listed in Table 2, four sheets of ceramics substrates (80×75 mm, with a thickness of 6 mm) with clean surfaces were dipped into 500 ml of the antibacterial sol-gel coating solutions from Examples 1-4 respectively, in a dip coater at ambient temperature under atmospheric pressure, to form a coating layer. The substrates were then dried in air for 12 min and subjected to thermal treatment to obtain antibacterial articles.

The thickness of the layer on each of the resulting antibacterial articles was measured by a gauge-meter or a scanning electron microscope (SEM), and the change of the content of each ingredient between the substrate to be coated and the coated substrate was recorded to determine the amount of the ingredient introduced into the coating layer. The results were listed in Table 2.

TABLE 2

Antibacterial Ceramics Article

| sample number coating solution | | ceramics 1# Example 1 | ceramics 2# Example 2 | ceramics 3# Example 3 | ceramics 4# Example 4 |
|---|---|---|---|---|---|
| dip coating time (second) | | 32 | 33 | 32 | 33 |
| thermal treatment | temperature (° C.) | 600 | 600 | 600 | 600 |
| | time (hour) | 1.5 | 1.5 | 1.5 | 1.5 |
| coated film | thickness (nm) | 138 | 290 | 169 | 235 |
| | Composition (wt. %) Film carrier | $TiO_2$ (47.58%) | $SiO_2$ (75.97%) | $TiO_2$ (66.27%) | $SiO_2$ (65.59%) |
| | Antibacterial ion | $Ag^+$ (46.95%) | $Ag^+$ (20.69%) | $Cu^{2+}$ (23.97%) | $Cu^{2+}$ (24.92%) |

Example 7

In this Example, the antibacterial properties of the articles of the present invention were tested.

An antibacterial test was taken on the sample glass 2# and ceramics 3# in accordance with the Enterprise Standard QB/T2591-2003.

A mould mixture was used in the test, which included *Aspergillus niger, Aspergillus terreus, Paecilomyces variotii, Penicillium funiculosum, Aureobacidium pullulans*, and *Chaetomium globosum*. The results shows that, for the mould mixture, glass 2# and ceramics 3# performed antibacterial grade 0.

Example 8

In this Example, the antibacterial properties of the articles of the present invention were tested.

An antibacterial test was taken on the sample glass 1# and ceramics 2# in accordance with JC/T897-2002. The results are as follows.

TABLE 3

Results of Antibacterial Tests

| Bacteria species | Inhibition rate (%) |
|---|---|
| *Staphylococcus aureus* | 99.08 |
| *Escherichia coli* | 99.92 |

The invention has been described with reference to some specific embodiments. The description, however, shall never be construed as limiting the scope of the invention. The scope and spirit of the invention will be defined in the following claims. It is obvious for a person skilled in the art that modifications and variations can be made to the invention without departing from the scope and spirit of the invention.

The invention claimed is:

1. An antibacterial sol-gel coating solution, prepared by a method consisting of:
    combining materials consisting of:
    0.1 to 45% by weight of the total solution of at least one substance selected from the group consisting of Ti- or Si-containing compounds capable of hydrolyzing to form a base film, wherein the Ti- or Si-containing compounds are selected from the group consisting of butyl titanate, isobutyl titanate, ethyl titanate, n-propyl titanate, isopropyl titanate, titanium tetrachloride, titanium trichloride, titanium dioxide nanoparticle, tetraethyl orthosilicate, tetramethyl orthosilicate, tetrapropyl orthosilicate, tetrabutyl silicate, tetraisopropyl orthosilicate, and tetraisobutyl silicate;
    a regulating agent capable of regulating the hydrolysis rate of the Ti- or Si-containing compounds selected from the group consisting of acetylacetone and dimethyl formamide;
    an organic solvent;
    0.001-15% by weight of the total solution of water; and
    10-25% by weight of at least one soluble compound of an antibacterial metal on the basis of the total weight of the solution, said antibacterial metal being selected from the group consisting of Ag, Cu, Mg, Sn, Fe, Co, and Ni;
    wherein the at least one substance selected from the group consisting of Ti- or Si-containing compounds, the regulating agent, and a portion of the organic solvent are first mixed to form a solution I, then the water and the rest of the organic solvent are mixed and added into solution I to form a dispersion II, and finally the at least one soluble compound of an antibacterial metal is added into dispersion II to form the antibacterial sol-gel coating solution.

2. The antibacterial sol-gel coating solution according to claim 1, prepared by using 0.001-25% of the regulating agent.

3. The antibacterial sol-gel coating solution according to claim 1, wherein the organic solvent is selected from the group consisting of diethyl ether, acetone, isopropanol, propanol, ethanol, methanol, butanol, isobutanol, and ethylene glycol.

4. A process for preparing an antibacterial sol-gel coating solution according to claim 1, consisting of the steps of
    dissolving, in at least one first organic solvent, the at least one substance selected from the group consisting of Ti- or Si-containing compounds capable of hydrolyzing to form a base film, and the regulating agent capable of regulating the hydrolysis rate of the Ti- or Si-containing compounds to form a solution I;
    mixing the at least one second organic solvent with the water and adding the resulting mixture into solution I to form a dispersion II;
    adding the at least one soluble compound of an antibacterial metal into dispersion II to form the antibacterial sol-gel coating solution.

5. The process according to claim 4, wherein the weight ratio of the organic solvent(s) used in the mixing step to that used in the dissolving step is in the range of 1:0.1-30.

6. The process according to claim 4, wherein in the mixing step, the weight ratio of the organic solvent(s) to water is in the range of 1:0.0001-20.

7. A process for producing an antibacterial article, comprising the steps of applying the antibacterial sol-gel coating solution of claim 1 on at least one surface of a substrate to form a coating layer, and subjecting the coating layer to drying and thermal treatment.

8. The process according to claim 7, wherein the substrate is covered by a mask on one surface or part of the surface before being dip-coated with the coating solution.

* * * * *